United States Patent
Ikegami et al.

(10) Patent No.: US 12,128,905 B2
(45) Date of Patent: Oct. 29, 2024

(54) DRIVER STATE ESTIMATION DEVICE, DRIVER STATE ESTIMATION METHOD, AND LEARNING METHOD

(71) Applicant: Mitsubishi Electric Corporation, Tokyo (JP)

(72) Inventors: Kimika Ikegami, Tokyo (JP); Takuji Morimoto, Tokyo (JP); Genta Yoshimura, Tokyo (JP); Shan Gao, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 277 days.

(21) Appl. No.: 17/615,749

(22) PCT Filed: Jun. 18, 2019

(86) PCT No.: PCT/JP2019/024093
§ 371 (c)(1),
(2) Date: Dec. 1, 2021

(87) PCT Pub. No.: WO2020/255252
PCT Pub. Date: Dec. 24, 2020

(65) Prior Publication Data
US 2022/0315011 A1    Oct. 6, 2022

(51) Int. Cl.
*B60W 40/09* (2012.01)
*G07C 5/04* (2006.01)

(52) U.S. Cl.
CPC ............... *B60W 40/09* (2013.01); *G07C 5/04* (2013.01)

(58) Field of Classification Search
CPC ......... B60W 40/09; B60W 2040/0872; B60W 2040/0818; B60W 2040/0827;
(Continued)

(56) References Cited

U.S. PATENT DOCUMENTS

| 2009/0234552 A1 | 9/2009 | Takeda et al. |
| 2010/0047744 A1 | 2/2010 | Miura |

(Continued)

FOREIGN PATENT DOCUMENTS

| JP | 2007-272834 A | 10/2007 |
| JP | 2009-301367 A | 12/2009 |

(Continued)

OTHER PUBLICATIONS

Zhen Gao et al., Driver Identification Based on Stop-and-Go Events Using Naturalistic Driving Data, 2018 11th International Symposium on Computational Intelligence and Design, p. 306-310 (Year: 2018).*

(Continued)

*Primary Examiner* — Ryan Rink
(74) *Attorney, Agent, or Firm* — Sughrue Mion, PLLC; Richard C. Turner

(57) ABSTRACT

An information collection unit collects information indicating a driving operation of a vehicle by a driver and a state of the vehicle changed by the driving operation, and outputs, among the collected information, information in a period from a start point at which a driving operation contributing to stop of the vehicle is performed to a stop start point in a stop state where a stop time of the vehicle continues for a predetermined time or more, as driving operation information. A state estimation unit acquires driver state information indicating a state of the driver from a learned learner on which machine learning has been performed so as to output the driver state information when the driving operation information is input, by inputting the driving operation information output from the information collection unit to the learner and performing arithmetic processing of the learner.

4 Claims, 4 Drawing Sheets

(58) Field of Classification Search
CPC . B60W 2040/0836; B60W 2040/0854; B60W 2040/0863; B60W 2040/0845
See application file for complete search history.

(56) References Cited

U.S. PATENT DOCUMENTS

| | | | | |
|---|---|---|---|---|
| 2020/0207358 | A1* | 7/2020 | Katz | G02B 27/0093 |
| 2020/0250982 | A1* | 8/2020 | Kim | G06V 40/20 |
| 2020/0269867 | A1* | 8/2020 | Hua | B60T 7/22 |
| 2021/0221404 | A1* | 7/2021 | Reiner | G06V 20/597 |
| 2022/0315010 | A1* | 10/2022 | Watanabe | A61B 5/14551 |
| 2024/0199086 | A1* | 6/2024 | Aoki | B60W 60/005 |

FOREIGN PATENT DOCUMENTS

| | | |
|---|---|---|
| JP | 2010-048655 A | 3/2010 |
| JP | 2012-254694 A | 12/2012 |

OTHER PUBLICATIONS

Chisato Shibata, et al., "Driver Characteristic Estimation Using Vehicle Behavior Data While Preceding Vehicle Decelerating", Information Processing Society of Japan, IPSJ SIG Technical Report, Mar. 2016, pp. 1-8, vol. 64, No. 11.
Yusuke Tanaka, et al., "Anomaly Driver State Detection from Vehicle BeVol. 44, No. 2, havior Data", Transactions of Society of Automotive Engineers of Japan, Mar. 2013, pp. 685-690.
International Search Report for PCT/JP2019/024093 dated Sep. 10, 2019.
Written Opinion for PCT/JP2019/024093 dated Sep. 10, 2019.
Notice of Reasons for Refusal dated Jun. 14, 2022 from the Japanese Patent Office in JP Application No. 2021-528498.
Communication dated Feb. 10, 2023 from the State Intellectual Property Office of P.R. of China in Application No. 201980097328.0.
Office Action dated Nov. 8, 2022 issued by the Japanese Patent Office in Japanese Application No. 2021-528498.

* cited by examiner

DRIVER STATE ESTIMATION DEVICE, DRIVER STATE ESTIMATION METHOD, AND LEARNING METHOD

CROSS REFERENCE TO RELATED APPLICATIONS

This application is a National Stage of International Application No. PCT/JP2019/024093 filed Jun. 18, 2019.

TECHNICAL FIELD

The present invention relates to a driver state estimation device, a driver state estimation method, and a learning method for a vehicle.

BACKGROUND ART

There has been proposed a driving support device that creates a driver model using data of a driving state when a driver is driving in a normal state, estimates a driving operation in the normal state using the created driver model, and determines the state of the driver from the estimated driving operation and an actual driving operation, thereby performing driving support (see, for example, Patent Literature 1).

CITATION LIST

Patent Literature

Patent Literature 1: JP 2007-272834 A

SUMMARY OF INVENTION

Technical Problem

In a conventional driving support device, it is necessary to create a driver model for each scene of an environment surrounding a host vehicle, such as a scene where the host vehicle is about to turn right from an exclusive right-turn lane at an intersection with a green light on a national road with three lanes on each side, there is an oncoming vehicle, and there is a pedestrian on a crosswalk. In a place such as an intersection, for example, there are various scenes depending on the position, number, and motion of each of oncoming vehicles and pedestrians. For this reason, it is difficult for the conventional driving support device to create a driver model capable of estimating a state of a driver depending on each of the various scenes.

The present invention has been made to solve the above problems, and an object of the present invention is to estimate a state of a driver regardless of a scene of an environment surrounding a host vehicle.

Solution to Problem

A driver state estimation device according to the present invention includes: processing circuitry to collect information indicating a driving operation of a vehicle by a driver and a state of the vehicle changed by the driving operation, and to output, among the collected information, information in a period from a start point at which a driving operation contributing to stop of the vehicle is performed to a stop start point in a stop state where a stop time of the vehicle continues for a predetermined time or more, as driving operation information; and to acquire driver state information indicating a state of the driver from a learned learner on which machine learning has been performed so as to output the driver state information when the driving operation information is input, by inputting the driving operation information to the learner and performing arithmetic processing of the learner.

Advantageous Effects of Invention

According to the present invention, vehicle stop that frequently occurs during driving is focused on, and the state of the driver is estimated by the learner using the information indicating a driving operation from deceleration to stop and the state of the vehicle changed by the driving operation. Consequently, it is possible to estimate the state of the driver regardless of the scene of the environment surrounding a host vehicle.

DESCRIPTION OF EMBODIMENTS

Hereinafter, in order to describe the present invention in more detail, a mode for carrying out the present invention will be described with reference to the accompanying drawings.

First Embodiment

Figure 1:
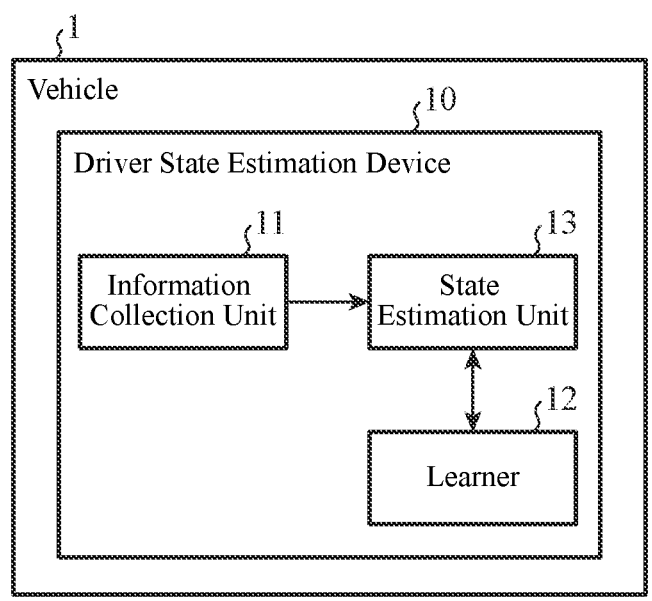
FIG. 1 is a block diagram illustrating a configuration example of a driver state estimation device according to a first embodiment.

FIG. 1 is a block diagram illustrating a configuration example of a driver state estimation device 10 according to a first embodiment. The driver state estimation device 10 according to the first embodiment includes an information collection unit 11, a learned learner 12, and a state estimation unit 13. The driver state estimation device 10 is mounted on a vehicle 1 and estimates that a driver of the vehicle 1 is in a state different from a normal state (hereinafter referred to as "abnormal state"). The normal state is a mental and physical state where the driver can drive the vehicle 1. The abnormal state is a careless state where the driver cannot concentrate on driving or is distracted, a dozing state where the driver is sleeping or feeling sleepy, a fatigue state, a state where the driver has an emotional problem such as being irritated, or the like. Note that in addition to estimating that the driver is in the abnormal state, the driver state estimation device 10 may estimate which state the driver is in among a careless state, a dozing state, a fatigue state, and a state where the driver has an emotional problem, and the like.

The information collection unit 11 collects information of the driving operation of the vehicle 1 by the driver and information indicating the state of the vehicle 1 changed by the driving operation. The driving operation information includes at least one of a brake operation amount, a steering operation amount, an accelerator operation amount, and the like applied to the vehicle 1 by the driver. The information indicating the state of the vehicle 1 includes at least one of a vehicle speed, a longitudinal acceleration, a lateral acceleration, a current position, and the like of the vehicle 1.

Note that the information collection unit 11 may collect information indicating the situation surrounding the vehicle 1 in addition to the driving operation information and the information indicating the state of the vehicle 1. The information indicating the surrounding situation includes information of surrounding vehicles, information of the positional relationship between the vehicle 1 and a white line, or the like, the information indicating the surrounding situation being acquired by, for example, a camera, various sensors, or a light detection and ranging (LiDAR) mounted on the vehicle 1, or vehicle-to-vehicle communication. The information of surrounding vehicles includes information indicating an inter-vehicle distance between the vehicle 1 and a preceding vehicle. The information of the positional relationship between the vehicle 1 and a white line includes information indicating a lane on which the vehicle 1 is traveling.

Among these collected pieces of information, the information collection unit 11 extracts information in a period from a start point at which the driving operation contributing to the stop of the vehicle 1 is performed to a stop start point in a state where the stop time of the vehicle 1 continues for a predetermined time or more (hereinafter, referred to as "stop state"), and outputs the extracted information to the state estimation unit 13 as the driving operation information.

Figure 2:
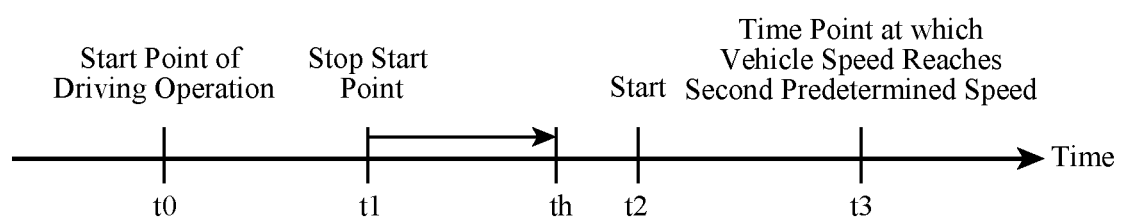
FIG. 2 is a diagram for explaining driving operation information that is input from an information collection unit to a state estimation unit.

FIG. 2 is a diagram for explaining driving operation information input from the information collection unit 11 to the state estimation unit 13. In the first embodiment, a scene is assured in which the vehicle 1 stops at an intersection in response to a signal. The stop refers to a state where the vehicle speed of the vehicle 1 is equal to or lower than a first predetermined speed. The first predetermined speed is a low speed close to 0 km/h.

In FIG. 2, a time t0 is a start point at which the driving operation contributing to the stop of the vehicle 1 is performed. The start point is, for example, a time when the driver performs a driving operation to stop the vehicle 1 or a time when the state of the vehicle 1 starts to change due to the driving operation performed by the driver to stop the vehicle 1, such as a change in an accelerator operation amount due to the driver releasing a foot from an accelerator pedal, an operation of a brake and a change in a brake operation amount due to stepping on a brake pedal, or a decrease in vehicle speed.

In FIG. 2, a time t1 is a stop start point in the stop state of the vehicle 1. The stop start point is a time when the stop state starts in the stop state where the stop time of the vehicle 1 continues for a predetermined time th or more. The stop time is a time from the time t1 in FIG. 2, which is the stop start point, to a time t2 in FIG. 2, which is a time point at which the vehicle 1 starts.

Note that among these pieces of collected information, the information collection unit 11 may extract information in a period from the start point at which the driving operation contributing to the stop of the vehicle 1 is performed to a time point at which the vehicle 1 in the stop state starts and reaches a predetermined vehicle speed, and outputs the extracted information to the state estimation unit 13 as the driving operation information. In FIG. 2, a time t3 is a time point at which the vehicle 1 in the stop state starts and reaches a second predetermined speed. The second predetermined speed may be equal to the first predetermined speed, or may be higher than the first predetermined speed.

The learner 12 is a learned model on which machine learning has been performed so as to output information indicating the state of the driver (hereinafter, referred to as "driver state information") when the driving operation information is input. The learner 12 may be provided, in advance, in the driver state estimation device 10 or may be acquired from the outside via a communication device or the like. Further, the learner 12 provided, in advance, in the driver state estimation device 10 may be replaced with another learner 12 acquired from the outside, halfway. In addition, the learner 12 may be the same regardless of the vehicle type, the driver, or the like of the vehicle 1, or may be learned depending on the vehicle type, the driver, or the like of the vehicle 1. Furthermore, the driver state estimation device 10 may include in advance a plurality of learners 12 learned for each tendency of a general driver's driving operation. In this case, the state estimation unit 13 to be described later may determine the tendency of the driving operation of the actual driver who gets on the vehicle 1 on the basis of the initial driving operation information of the driver, and select and use the learner 12 suitable for the tendency of the driving operation of the driver from among the plurality of learners 12. Alternatively, the state estimation unit 13 may select driver state information to be adopted by performing a majority decision or by performing a logical operation, from among a plurality of pieces of driver state information acquired from the plurality of learners 12.

The state estimation unit 13 acquires the driver state information indicating the driving state of the vehicle 1 from the learner 12, by inputting the driving operation information output from the information collection unit 11 to the learned learner 12 and performing arithmetic processing of the learner 12. The driver state information is information indicating whether the driver is in a normal state or an abnormal state. Further, in addition to the information indicating whether the driver is in the normal state or the abnormal state, the driver state information may include information indicating which state the driver is in among a careless state, a dozing state, a fatigue state, and a state where the driver has an emotional problem, and the like.

For example, in "Anomaly Driver State Detection from Vehicle Behavior Data" (Yusuke Tanaka and Takashi Bando, Transactions of Society of Automotive Engineers of Japan, 2013, vol. 44, no. 2, 685-690), a method is proposed in which it is assumed that a larger variation or delay occurs in a driving operation in a case where the driver falls into an abnormal state as compared with a driving operation in a normal state, and the abnormal state of the driver is estimated on the basis of the behavior of the vehicle 1.

In addition, "Driver Characteristic Estimation Using Vehicle Behavior Data While Preceding Vehicle Decelerating" (Chisato Shihata and three others, IPSJ SIG Technical Report, 2016, vol. 64, no. 11, 1-8) indicates that there is a correlation between the vehicle behavior when the preceding vehicle decelerates and the characteristic of the driver, and suggests that the characteristic of the driver can be estimated from the vehicle behavior.

As described above, it is conventionally clear that the driving operation and the vehicle behavior as a result of the driving operation vary depending on the state of a driver.

The driving operation of stopping the vehicle due to a red light or temporary stop is an operation that frequently occurs during driving, and has uniformity in operation and less disturbance with respect to the operation as compared with the operation for each scene of the environment surrounding a host vehicle. Consequently, the driver state estimation device 10 according to the first embodiment accurately estimates the abnormal state of the driver by particularly focusing on the driving operation contributing to the vehicle stop and the state of the vehicle changed by the driving operation. In addition, since the number of times of occurrence of the driving operation contributing to the vehicle stop is large, the creation efficiency of the learner 12 is also good. On the other hand, in the conventional technique as described in Patent Literature 1, the driver model corresponding to the type of a scene is created by focusing on a scene instead of a driving operation. However, in a place where various scenes occur such as an intersection, the number of times that the same type of scene appears is small, and there is no consistency in operation between scenes. Therefore, it is difficult in the conventional technique to create a driver model capable of estimating the state of the driver depending on various scenes.

Next, the operation of the driver state estimation device 10 will be described.

Figure 3:
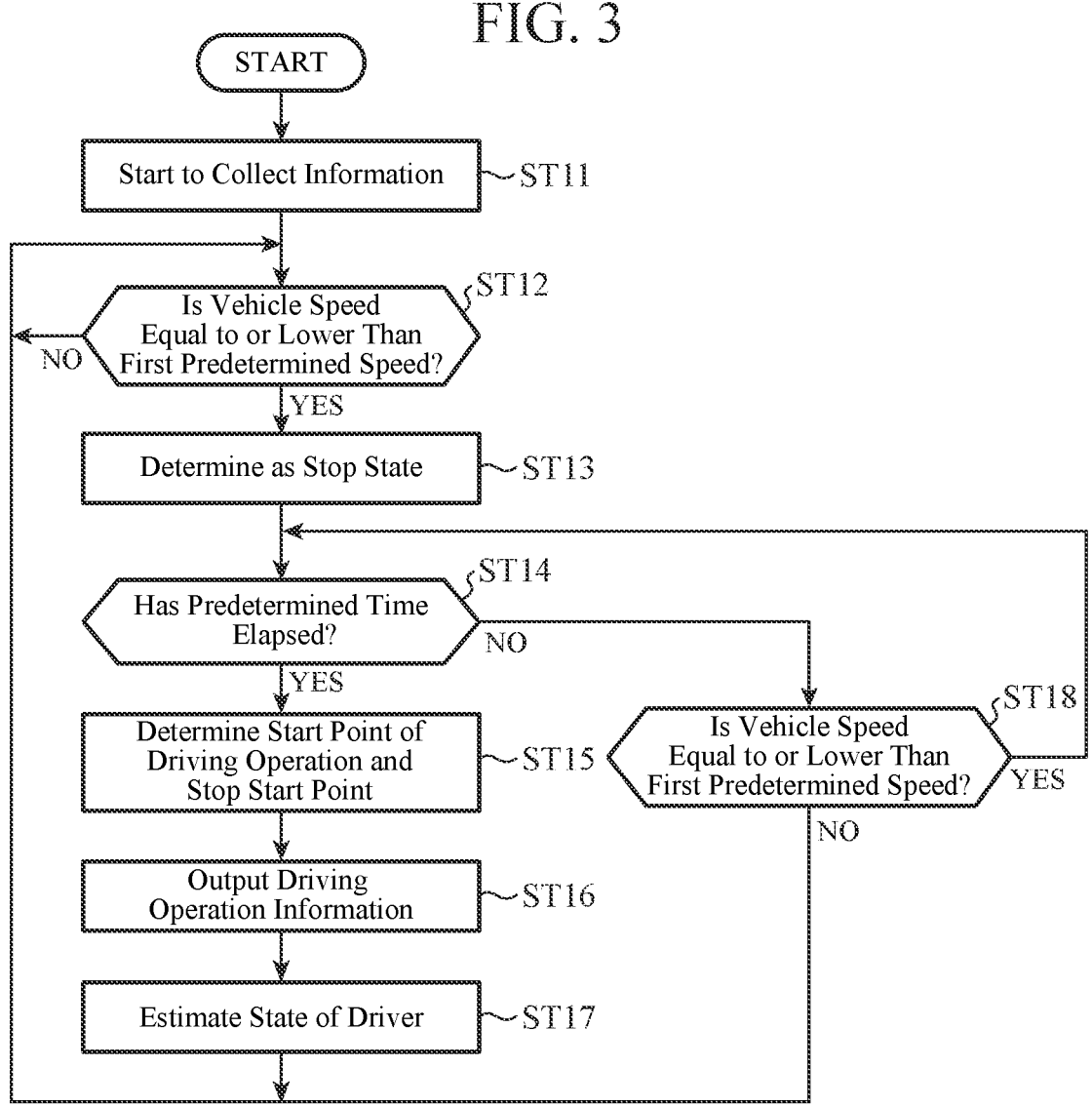
FIG. 3 is a flowchart illustrating an operation example of the driver state estimation device according to the first embodiment.

FIG. 3 is a flowchart illustrating an operation example of the driver state estimation device 10 according to the first embodiment. Note that the driving operation information in FIG. 3 is not information in a period from the start point (the time t0 FIG. 2) at which the driving operation contributing to the stop of the vehicle 1 is performed to the time point (the time t3 in FIG. 2) at which the vehicle 1 in the stop state starts and reaches the second predetermined speed, but information in a period from the start point (the time t0 in FIG. 2) at which the driving operation contributing to the stop of the vehicle 1 is performed to the stop start point (the time t1 in FIG. 2) in the stop state where the stop time of the vehicle 1 continues fora predetermined time (the time th in FIG. 2) or longer.

In step ST11, the information collection unit 11 starts processing of collecting, from the vehicle 1, information of a driving operation, information indicating the state of the vehicle 1 changed by the driving operation, and information indicating the situation surrounding the vehicle 1.

In step ST12, the information collection unit 11 determines whether or not the vehicle speed collected as one of the information indicating the state of the vehicle 1 is equal to or lower than a first predetermined speed.

If the vehicle speed is equal to or lower than the predetermined speed ("YES" in step ST12), the information collection unit 11 determines, in step ST13, that the vehicle 1 is in a stop state. On the other hand, if the vehicle speed is not equal to or lower than the first predetermined speed ("NO" in step ST12), the processing performed by the information collection unit 11 returns to step ST12.

In step ST14, the information collection unit 11 determines whether or not the predetermined time th has elapsed since the time point at which it is determined as the stop state in step ST13.

If the predetermined time th has elapsed while the vehicle speed remains equal to or lower than the first predetermined speed ("YES" in step ST14), the information collection unit 11 determines, in step ST15, the start point (the time t0 in FIG. 2) at which the driving operation contributing to the stop of the vehicle 1 is performed, on the basis of the information collected in step ST11. In addition, the information collection unit 11 determines the time point at which it is determined as the stop state in step ST13, as the stop start point (the time t1 in FIG. 2) in the stop state of the vehicle 1. On the other hand, if the predetermined time (the time th in FIG. 2) has not elapsed ("NO" in step ST14), in step ST18, the information collection unit 11 determines whether or not the vehicle speed is equal to or lower than the first predetermined speed. If the vehicle speed is equal to or lower than the first predetermined speed ("YES" in step ST18), the processing performed by the information collection unit 11 returns to step ST14, and if the vehicle speed is not equal to or lower than the first predetermined speed ("NO" in step ST18), the processing performed by the information collection unit 11 returns to step ST12.

In step ST16, the information collection unit 11 outputs, as driving operation information, information collected between the start point of the driving operation contributing to the stop of the vehicle 1 and the stop start point, the start point and the stop start point being determined in step ST15.

In step ST17, the state estimation unit 13 inputs the driving operation information output from the information collection unit 11 in step ST16 to the learner 12 and performs arithmetic processing of the learner 12, thereby estimating the state of the driver of the vehicle 1. The state estimation unit 13 then acquires driver state information indicating the state of the driver, from the learner 12.

The driver state information acquired by the state estimation unit 13 from the learner 12 is used for determining whether or not to switch the driving mode of the vehicle 1 from manual driving to automated driving, determining whether or not to change the level of the automated driving, determining whether or not to prompt the driver to take a break during the manual driving (that is, to prompt the driver to stop the vehicle), determining whether or not to switch the manual driving by the occupant of the vehicle 1 to remote control by an operator outside the vehicle, or the like.

Note that the information input to the learner 12 by the state estimation unit 13 is not limited to the information of the driving operation, the information indicating the state of the vehicle 1 changed by the driving operation, and the information indicating the situation surrounding the vehicle 1, these pieces of information being collected by the information collection unit 11.

Here, the information of the driving operation, the information indicating the state of the vehicle 1 changed by the driving operation, and the information indicating the situation surrounding the vehicle 1, these pieces of information being collected by the information collection unit 11, are referred to as "first driving operation information". The state estimation unit 13 may input the first driving operation information to the learner 12, may input second driving operation information instead of the first driving operation information to the learner 12, or may input both the first driving operation information and the second driving operation information to the learner 12.

The second driving operation information is information derived from the first driving operation information. For example, in a case where the first driving operation information is a vehicle speed, the acceleration derived by differentiating the vehicle speed is the second driving operation information.

In the above example, the functions of the information collection unit 11, the learner 12, and the state estimation unit 13 are integrated in the driver state estimation device 10 mounted on the vehicle 1. However, some or all of the functions may be provided in a server device on a network. For example, the driver state estimation device 10 includes an on-vehicle device including the information collection unit 11, and a server device including the learner 12 and the state estimation unit 13, In this case, the driving operation information is output from the information collection unit 11 in the on-vehicle device to the state estimation unit 13 in the server device via a communication device or the like, and the driver state information is estimated in the state estimation unit 13 in the server device. The driver state information is output from the state estimation unit 13 in the server device to the on-vehicle device via the communication device or the like.

Next, a learning device 20 that performs machine learning of the learner 12 included in the driver state estimation device 10 will be described.

Figure 4:
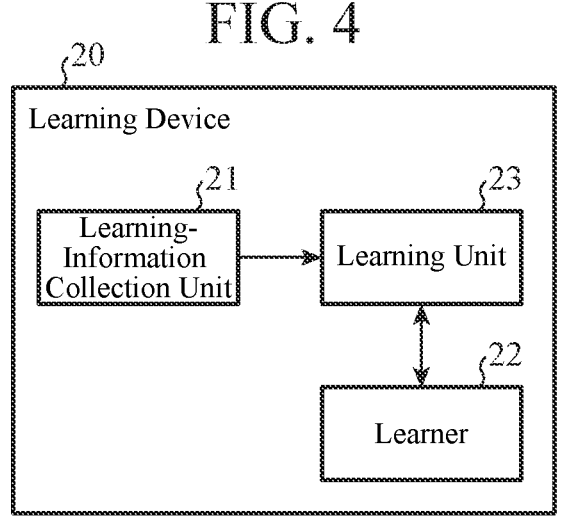
FIG. 4 is a block diagram illustrating a configuration example of a learning device according to the first embodiment.
Figure 5:
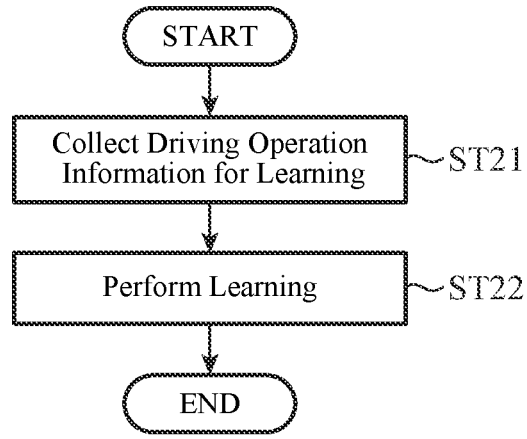
FIG. 5 is a flowchart illustrating an operation example of the learning device according to the first embodiment.

FIG. 4 is a block diagram illustrating a configuration example of the learning device 20 according to the first embodiment. The learning device 20 according to the first embodiment includes a learning-information collection unit 21, a learner 22, and a learning unit 23. FIG. 5 is a flowchart illustrating an operation example of the learning device 20 according to the first embodiment.

In step ST21, the learning-information collection unit 21 collects driving operation information used for machine learning of the learner 12. Similarly to the driving operation information input from the information collection unit 11 to the state estimation unit 13, the driving operation information collected by the learning-information collection unit 21 includes information indicating a driving operation of a vehicle by a driver and the state of the vehicle changed by the driving operation, in a period from a start point at which the driving operation contributing to stop of the vehicle is performed to a stop start point in a stop state where the stop time of the vehicle continues for a predetermined time or more. Furthermore, the driving operation information collected by the learning-information collection unit 21 may include information indicating a situation surrounding the vehicle, in addition to the information of the driving operation of the vehicle by the driver and the information indicating the state of the vehicle changed by the driving operation. Moreover, the driving operation information collected by the learning-information collection unit 21 may be information in a period from the start point at which the driving operation contributing to the stop of the vehicle is performed to a time point at which the vehicle in the stop state starts and reaches a predetermined vehicle speed. Further, the driving operation information collected by the learning-information collection unit 21 may be information corresponding to the first driving operation information or may be information corresponding to the second driving operation information.

In step ST22, the learning unit 23 inputs the driving operation information collected by the learning-information collection unit 21 to the learner 22, and performs machine learning of the learner 22. The learner 22 on which machine learning has been performed is the learned learner 12 to be used by the driver state estimation device 10.

Note that the learning device 20 may be provided in the same vehicle 1 as that having the driver state estimation device 10, or may be provided inside the driver state estimation device 10. In the case of these configurations, the learning device 20 can easily perform the online learning of the learner 22 using the driving operation information collected from the vehicle 1 on which the driver state estimation device 10 is mounted.

In a case where the learning device 20 is provided outside the vehicle 1, the learning device 20 may perform machine learning of the learner 22 by periodically collecting driver state information from the driver state estimation device 10 in the vehicle 1 via a communication device or the like, and output the learned learner 22 to the driver state estimation device 10.

In addition, the vehicle and the driver that are the information collection target of the learning-information collection unit 21 may be the vehicle 1 on which the driver state estimation device 10 is mounted and the driver thereof, in which the state estimation device 10 uses, as the learned learner 12, the learner 22 on which machine learning has been performed by the learning device 20, or may be a vehicle other than the vehicle 1 and a driver thereof.

In a case where supervised machine learning is performed, the learning unit 23 applies a correct answer label to the driving operation information input to the learner 22. The number of the correct answer labels may be two indicating the normal state and the abnormal state of the driver, or may be three or more indicating a plurality of respective stages obtained by classifying the normal state, the abnormal state and a state therebetween into the plurality of stages. A method of generating driving operation information to which the correct answer label of the abnormal state has been applied is not limited herein, but for example, the following method is provided. For example, the learning unit 23 acquires driving operation information in an abnormal state created in a pseudo manner and applies the correct answer label to the driving operation information. Alternatively, the learning unit 23 may determine the state of a driver who is driving by using the biological information of the driver measured by a biological sensor, and apply the determination result to the driving operation information as the correct answer label. For example, in a case where the biological sensor measures the pulse of the driver, the learning unit 23 determines whether or not the driver is in a dozing state, a fatigue state, or the like on the basis of the pulse. Alternatively, the learning unit 23 may determine the state of the driver who is driving by using the face image of the driver captured by a camera, and apply the determination result to the driving operation information as the correct answer label. For example, the learning unit 23 may determine whether or not the driver is in the dozing state by detecting the eye opening degree of the driver from the face image, or may determine whether or not the driver is in the dozing state by detecting the expression of the driver.

Figure 6A:
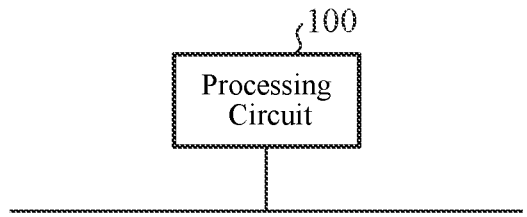
FIGS. 6A and 6B are diagrams each illustrating a hardware configuration example of the driver state estimation device according to the first embodiment.
Figure 6B:
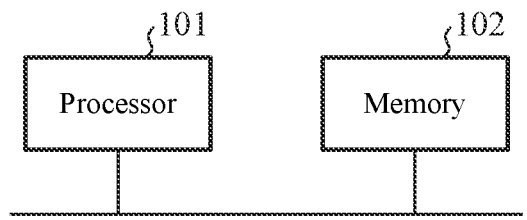

FIGS. 6A and 6B are diagrams each illustrating a hardware configuration example of the driver state estimation device 10 according to the first embodiment. The functions of the information collection unit 11, the learner 12, and the state estimation unit 13 in the driver state estimation device 10 are implemented by a processing circuit. That is, the driver state estimation device 10 includes a processing circuit for implementing the functions. The processing circuit may be a processing circuit 100 as dedicated hardware, or may be a processor 101 that executes a program stored in a memory 102.

As illustrated in FIG. 6A, in a case where the processing circuit is dedicated hardware, the processing circuit 100 corresponds to, for example, a single circuit, a composite circuit, a programmed processor, a parallel programmed processor, an application specific integrated circuit (ASIC), a field programmable gate array (FPGA), or a combination thereof. The functions of the information collection unit 11, the learner 12, and the state estimation unit 13 may be implemented by a plurality of the processing circuits 100, or the functions of the respective units may be collectively implemented by one processing circuit 100.

As illustrated in FIG. 6B, in a case where the processing circuit is the processor 101, the functions of the information collection unit 11, the learner 12, and the state estimation unit 13 are implemented by software, firmware, or a combination of software and firmware. The software or firmware is described as a program and stored in the memory 102. The processor 101 implements the function of each unit by reading and executing the program stored in the memory 102. That is, the driver state estimation device 10 includes the memory 102 for storing a program that results in performance of the steps illustrated in the flowchart of FIG. 3 when executed by the processor 101. Furthermore, it can also be said that this program causes a computer to perform procedures or methods performed by the information collection unit 11, the learner 12, and the state estimation unit 13.

Note that some of the functions of the information collection unit 11, the learner 12, and the state estimation unit 13 may be implemented by dedicated hardware, and some of the functions may be implemented by software or firmware. As described above, the processing circuit in the driver state estimation device 10 can implement the functions described above by hardware, software, firmware, or a combination thereof.

Figure 7A:
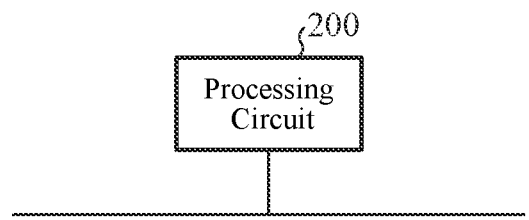
FIGS. 7A and 7B are diagrams each illustrating a hardware configuration example of the learning device according to the first embodiment.
Figure 7B:
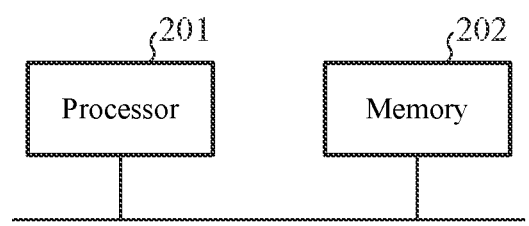

FIGS. 7A and 7B are diagrams each illustrating a hardware configuration example of the learning device 20 according to the first embodiment. The functions of the learning-information collection unit 21, the learner 22, and the learning unit 23 in the learning device 20 are implemented by a processing circuit. That is, the learning device 20 includes a processing circuit for implementing the functions. The processing circuit may be a processing circuit 200 as dedicated hardware, or may be a processor 201 that executes a program stored in a memory 202.

As illustrated in FIG. 7A, in a case where the processing circuit is dedicated hardware, the processing circuit 200 corresponds to, for example, a single circuit, a composite circuit, a programmed processor, a parallel programmed processor, ASIC, FPGA, or a combination thereof. The functions of the learning-information collection unit 21, the learner 22, and the learning unit 23 may be implemented by a plurality of the processing circuits 200, or the functions of the respective units may be collectively implemented by one processing circuit 200.

As illustrated in FIG. 7B, in a case where the processing circuit is the processor 201, the functions of the learning-information collection unit 21, the learner 22, and the learning unit 23 are implemented by software, firmware, or a combination of software and firmware. The software or firmware is described as a program and stored in the memory 202. The processor 201 implements the function of each unit by reading and executing the program stored in the memory 202. That is, the learning device 20 includes the memory 202 for storing a program that results in performance of the steps illustrated in the flowchart of FIG. 5 when executed by the processor 201. Furthermore, it can also be said that this program causes a computer to perform procedures or methods performed by the learning-information collection unit 21, the learner 22, and the learning unit 23.

Note that some of the functions of the learning-information collection unit 21, the learner 22, and the learning unit 23 may be implemented by dedicated hardware, and some of the functions may be implemented by software or firmware. As described above, the processing circuit in the learning device 20 can implement the functions described above by hardware, software, firmware, or a combination thereof.

The processor 101, 201 is a central processing unit (CPU), a processing device, an arithmetic device, a microprocessor, or the like.

The memory 102, 202 may be a nonvolatile or volatile semiconductor memory such as a random access memory (RAM), a read only memory (ROM), an erasable programmable ROM (EPROM), or a flash memory, may be a magnetic disk such as a hard disk or a flexible disk, or may be an optical disk such as a compact disc (CD) or a digital versatile disc (DVD).

As described above, the driver state estimation device 10 according to the first embodiment includes the information collection unit 11 and the state estimation unit 13. The information collection unit 11 collects information indicating a driving operation of the vehicle 1 by a driver and the state of the vehicle 1 changed by the driving operation, and outputs, among the collected information, information in a period from a start point at which the driving operation contributing to the stop of the vehicle 1 is performed to a stop start point in a stop state where the stop time of the vehicle 1 continues for a predetermined time or more, as driving operation information. The state estimation unit 13 acquires driver state information indicating a state of the driver from the learned learner 12 on which machine learning has been performed so as to output the driver state information when the driving operation information is input, by inputting the driving operation information output from the information collection unit 11 to the learner 12 and performing arithmetic processing of the learner 12. With this configuration, the driver state estimation device 10 focuses on vehicle stop that frequently occurs during driving, and estimates the state of the driver by the learner 12 using the information indicating a driving operation from deceleration to stop and the state of the vehicle 1 changed by the driving operation. Consequently, it is possible to estimate the state of the driver regardless of the scene of the environment surrounding a host vehicle.

Further, according to the first embodiment, the driving operation information may be the first driving operation information that is at least one of a brake operation, a steering operation, an accelerator operation, and a vehicle speed for the vehicle 1, or the second driving operation information derived from the first driving operation information. As the number of types of information to be input to the learner 12 increases, the driver state estimation device 10 can estimate the state of the driver more accurately.

Moreover, according to the first embodiment, the driving operation information may include, among the information collected by the information collection unit 11, information in a period from the start point at which the driving operation contributing to the stop of the vehicle 1 is performed to a time point at which the vehicle 1 in the stop state starts and reaches a predetermined vehicle speed. As the time to collect the information to be input to the learner 12 is longer, the driver state estimation device 10 can estimate the state of the driver more accurately.

Furthermore, the learning device 20 according to the first embodiment includes the learning-information collection unit 21 and the learning unit 23. The learning-information collection unit 21 collects, as the driving operation information, information indicating the driving operation of the vehicle by the driver and the state of the vehicle changed by the driving operation in a period from the start point at which the driving operation contributing to the stop of the vehicle is performed to the stop start point in the stop state where the stop time of the vehicle continues for a predetermined time or more. The learning unit 23 causes the learner 22 to perform machine learning so as to output driver state information indicating the state of the driver when the driving operation information is input. With this configuration, the learning device 20 can configure the learner 22 capable of estimating the state of the driver regardless of the scene of the environment surrounding the host vehicle.

Note that, in the present invention, any component of the embodiment can be modified or omitted within the scope of the invention.

INDUSTRIAL APPLICABILITY

Since the driver state estimation device according to the present invention estimates the state of a driver during driving, the driver state estimation device is suitable for, for example, a driver state estimation device that is mounted on an automated driving vehicle that switches between automated driving and manual driving depending on the state of the driver.

REFERENCE SIGNS LIST

1: vehicle, 10: driver state estimation device, 11: information collection unit, 12: learner, 13: state estimation unit, 20: learning device, 21: learning-information collection unit, 22: learner, 23: learning unit, 100, 200: processing circuit, 101, 201: processor, 102, 202: memory

The invention claimed is:

1. A driver state estimation device comprising:
processing circuitry to collect information indicating a driving operation of a vehicle by a driver and a state of the vehicle changed by the driving operation;
in response to a stop state of the vehicle lasting for a predetermined time or longer, to output, among the collected information, information collected in a collection period between an initiation of a driving operation leading to stop of the vehicle and a stop start point of the stop state of the vehicle, as driving operation information;
to acquire driver state information indicating a state of the driver from a learned learner on which machine learning has been performed in such a manner as to output the driver state information when the driving operation information is input, by inputting the driving operation information to the learner and performing arithmetic processing of the learner; and
to control a brake operation of the vehicle based on the driver state information.

2. The driver state estimation device according to claim 1, wherein the driving operation information is first driving operation information that is at least one of a brake operation, a steering operation, an accelerator operation, and a vehicle speed for the vehicle, or second driving operation information that is derived from the first driving operation information.

3. A driver state estimation method comprising:
collecting information indicating a driving operation of a vehicle by a driver and a state of the vehicle changed by the driving operation;
in response to a stop state of the vehicle lasting for a predetermined time or longer, outputting, among the collected information, information collected in a collection period between an initiation of a driving operation leading to stop of the vehicle and a stop start point of the stop state of the vehicle, as driving operation information;
acquiring driver state information indicating a state of the driver from a learned learner on which machine learning has been performed in such a manner as to output the driver state information when the driving operation information is input, by inputting the driving operation information to the learner and performing arithmetic processing of the learner; and
controlling a brake operation of the vehicle based on the driver state information.

4. A learning method comprising:
collecting information indicating a driving operation of a vehicle by a driver and a state of the vehicle changed by the driving operation; and
in response to a stop state of the vehicle lasting for a predetermined time or longer, outputting, among the collected information, information collected in a collection period between an initiation of a driving operation leading to stop of the vehicle and a stop start point of the stop state of the vehicle, as driving operation information;
causing a learner to perform machine learning in such a manner as to output driver state information indicating a state of the driver when the driving operation information is input; and
causing the vehicle to control a brake operation based on the driver state information.

* * * * *